(12) United States Patent
Masaoka et al.

(10) Patent No.: US 7,842,001 B2
(45) Date of Patent: Nov. 30, 2010

(54) AUTOMATIC PRIMING METHOD

(75) Inventors: Katsunori Masaoka, Hiroshima (JP); Takashi Doi, Hiroshima (JP); Kaoru Kushiyama, Hiroshima (JP)

(73) Assignee: JMS Co., Hiroshima (JP)

( * ) Notice: Subject to any disclaimer, the term of this patent is extended or adjusted under 35 U.S.C. 154(b) by 561 days.

(21) Appl. No.: 11/794,639

(22) PCT Filed: Jan. 6, 2006

(86) PCT No.: PCT/JP2006/000059

§ 371 (c)(1),
(2), (4) Date: Jul. 2, 2007

(87) PCT Pub. No.: WO2006/073166

PCT Pub. Date: Jul. 13, 2006

(65) Prior Publication Data

US 2010/0042036 A1 Feb. 18, 2010

(30) Foreign Application Priority Data

Jan. 7, 2005 (JP) .............................. 2005-002432

(51) Int. Cl.
| | |
|---|---|
| *A61M 37/00* | (2006.01) |
| *B01D 24/46* | (2006.01) |
| *B01D 29/62* | (2006.01) |
| *B01D 33/44* | (2006.01) |
| *B01D 35/00* | (2006.01) |
| *B01D 41/00* | (2006.01) |
| *A61M 1/00* | (2006.01) |

(52) U.S. Cl. ..................... 604/6.01; 604/5.04; 604/6.11; 604/6.13; 210/793; 210/108; 210/143; 210/646; 422/44

(58) Field of Classification Search ................ 604/6.06, 604/5.04, 6.11, 6.13; 210/793, 108, 143, 210/646; 422/44
See application file for complete search history.

(56) References Cited

U.S. PATENT DOCUMENTS 4,552,721 A * 11/1985 Fentress et al. ............... 422/28
4,707,335 A * 11/1987 Fentress et al. ............... 422/44

(Continued)

FOREIGN PATENT DOCUMENTS

JP           63-315061         12/1988

(Continued)

*Primary Examiner*—Leslie R. Deak
*Assistant Examiner*—Adam Marcetich
(74) *Attorney, Agent, or Firm*—Jordan and Hamburg LLP

(57) ABSTRACT

An automatic priming method in which an arterial-side chamber is maintained in a normal position during priming, as in a case of dialysis treatment, and in which forward and backward rotations of a blood pump are employed, and a speed of rotation, in particular, backward rotation, is adjusted to be low, so that air or the like is reliably prevented from entering a dialyzer. The priming method for use in a blood purification circuit in which priming is conducted by supplying physiological saline into a circulation circuit formed by connecting an arterial blood circuit with a venous blood circuit includes filling the venous blood circuit with a priming solution (physiological saline), discharging the priming solution for cleaning the arterial blood circuit, conducting a treatment in a direction opposite to the overflow step, which may be followed by a forward direction re-circulation step, and re-circulating in a forward direction.

9 Claims, 3 Drawing Sheets

U.S. PATENT DOCUMENTS

| | | | | |
|---|---|---|---|---|
| 4,828,543 | A * | 5/1989 | Weiss et al. | 604/6.09 |
| 4,867,739 | A * | 9/1989 | Kawano | 604/5.04 |
| 5,520,640 | A * | 5/1996 | Utterberg | 604/80 |
| 5,650,071 | A * | 7/1997 | Brugger et al. | 210/646 |
| 5,776,091 | A | 7/1998 | Brugger et al. | |
| 5,863,421 | A * | 1/1999 | Peter et al. | 210/134 |
| 5,932,103 | A * | 8/1999 | Kenley et al. | 210/646 |
| 5,951,870 | A | 9/1999 | Utterberg | |
| 6,132,616 | A * | 10/2000 | Twardowski et al. | 210/646 |
| 6,165,149 | A * | 12/2000 | Utterberg et al. | 604/5.01 |
| 6,187,198 | B1 | 2/2001 | Utterberg | |
| 6,464,878 | B2 * | 10/2002 | Utterberg | 210/645 |
| 7,166,084 | B2 * | 1/2007 | Utterberg | 604/4.01 |
| 2001/0039441 | A1 * | 11/2001 | Ash | 607/106 |
| 2003/0163077 | A1 * | 8/2003 | Kim et al. | 604/5.01 |
| 2005/0230314 | A1 * | 10/2005 | Kim et al. | 210/646 |

FOREIGN PATENT DOCUMENTS

| | | |
|---|---|---|
| JP | 5-19076 | 5/1993 |
| JP | 8-38597 | 2/1996 |
| JP | 11-506962 | 6/1999 |
| JP | 2001-520101 | 10/2001 |
| WO | WO-96/40320 | 12/1996 |

* cited by examiner

AUTOMATIC PRIMING METHOD

TECHNICAL FIELD

The present invention relates to a method of automatically priming a blood purification circuit including a blood purifier connected to a blood circuit.

BACKGROUND ART

In general, before using a blood purification circuit for dialysis, there is performed a treatment of eliminating foreign substances and air existing in the blood circuit by introducing a priming liquid (generally, physiological saline is used) to fill a blood circuit therewith, that is, a priming treatment.

In a conventional dialysis apparatus, physiological saline is used to manually conduct priming of the blood circuit. However, recently, the priming is conducted by using an automatic priming apparatus.

As the automatic priming apparatus, Patent Document 1 discloses the following: that is, an artificial dialysis apparatus including a blood circuit having a dialyzer, which is provided with a blood pump, in which an arterial blood circuit and a venous blood circuit are connected to each other to form a circulation circuit, an overflow tube and an opening and closing means are provided above a drip chamber of the blood circuit, and the blood pump is actuated in a state where the opening and closing means of the tube is opened to allow a priming liquid to circulate through the circuit and the priming liquid is supplied from a priming liquid storage container to the circulation circuit at a predetermined flow rate, thereby discharging a part of the priming liquid from the overflow tube and conducting the priming.

However, in a case where the priming is conducted by this method, air remains in an inlet-side drip chamber. Therefore, there arises a problem in that the drip chamber cannot be filled with the priming liquid (physiological saline).

In order to solve the problem, Patent Document 2 suggests an automatic priming method for a blood purification circuit, in which an arterial-side chamber (corresponding to the inlet-side drip chamber of Patent Document 1 described above) provided in a blood circuit is installed while being directed upside down and priming is conducted. In a case where the method is adopted, at a time of a dialysis treatment performed afterwards, there is required an operation of returning the installation direction to an original direction. Without this operation, it is impossible to perform trapping of bubbles, which is one object of the drip chamber.

Patent Document 1: Japanese Utility Model Examined Publication No. Hei 05-19076

Patent Document 2: Japanese Patent Application Laid-open No. Hei 08-38597

DISCLOSURE OF THE INVENTION

Problem to be Solved by the Invention

In consideration of the conventional technique as described above, it is an object of the present invention to provide an automatic priming method by which priming is conducted while keeping, in the automatic priming, an arterial-side chamber in a normal position as in a case of dialysis treatment, forward and backward rotations of a blood pump are employed, and a speed of rotation, in particular, backward rotation is adjusted (to be relatively low) so that air or the like is reliably prevented from entering a dialyzer and is eliminated.

Means for Solving the Problem

In order to achieve the above-mentioned object, the present invention provides a priming method in which a connection portion 1 of an arterial blood circuit L1 and a connection portion 2 of a venous blood circuit L2 are connected to form a circulation circuit in which a blood pump P1, an arterial chamber C2, a blood purifier (dialyzer) D, and a venous chamber C1 are arranged in the stated order, the venous chamber C1 being connected to an overflow line O, a side of the venous blood circuit being provided with a valve PV2, the arterial blood circuit L1 having a system in which a storage container S for storing a physiological saline S1 and a supply pipe K are connected to each other at a branch portion a, the method including: (1) an early injection step for a priming liquid (physiological saline); (2) an overflow step; and (3) a reverse direction re-circulation step, the method being characterized in that, those steps may be followed by a forward direction re-circulation step (valve 1 and valve 2 are opened, blood pump P1 is operated to rotate forward to supply a priming liquid and while circulation is performed, an excessive liquid is discharged through overflow line O, that is, a step according to claim 5), and as needed, (4) a forward direction circulation step is performed.

Note that, the supply pipe K may be provided with a detector E, a valve PV3 for opening and closing the supply pipe, and the like. The valves and the blood pump P1 may be connected to an operation control portion F for controlling operations of those.

EFFECT OF THE INVENTION

In the present invention, by the above-mentioned priming method, since an installation direction of the chamber is set to that in the normal position, unlike in a case where the chamber is set in an opposite position, there is no problem of forgetting an operation of returning the position of the chamber to the normal position when performing a dialysis treatment. Further, forward and backward rotations of a blood pump are employed, and a speed of rotation, in particular, backward rotation is adjusted (to be relatively low) so that air is reliably prevented from entering a dialyzer.

Moreover, steps from an early injection step to a circulation step can be automatically set by a program in advance. Further, by making a blood circuit as a cassette, an inexpensive circuit can be provided.

Figure 1:
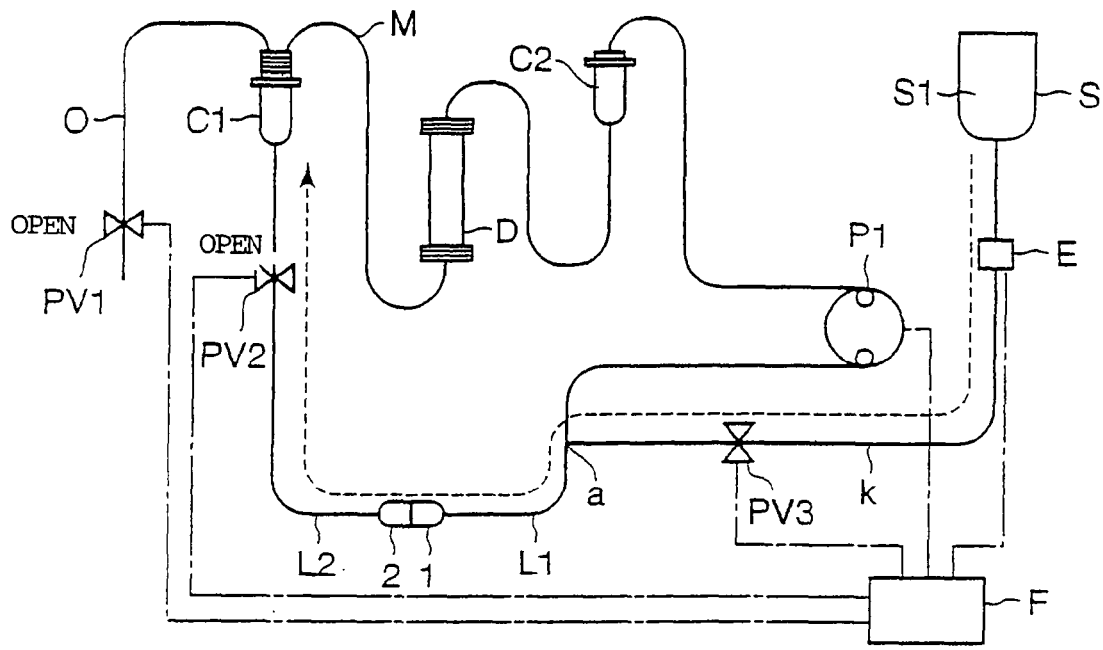
FIG. 1 is a schematic diagram showing an early injection step according to the present invention.

DESCRIPTION OF REFERENCE SYMBOLS a saline line branch portion
C1 venous chamber
C2 arterial chamber D blood dialyzer (dialyzer)
E liquid shortage detector
F operation control portion
G border surface
K supply pipe
M main line
L1 arterial blood circuit
L2 venous blood circuit
O overflow line
P1 blood pump
PV1 valve 1
PV2 valve 2
PV3 valve 3
S physiological saline storage
S1 physiological saline
1 arterial-side connection portion
2 venous-side connection portion

BEST MODE FOR CARRYING OUT THE INVENTION

Hereinafter, a detailed description will be made of an automatic priming method according to the present invention in an embodiment with reference to the drawings.

(a) FIG. 1 (filling of a line from a branch point a to a venous chamber C1 with physiological saline) shows an early injection step of filling a venous blood circuit L2 with the physiological saline of the present invention. In the step, a blood pump P1 is stopped, an overflow line opening and closing means PV1 (valve 1) and a venous circuit closing means PV2 (valve 2) are opened. By a drop pressure in a physiological saline storage container S, the physiological saline fills a venous chamber C1 through a physiological saline line branch portion a and the venous circuit closing means PV2, and is discharged together with bubbles through an overflow line O and the overflow line opening and closing means PV1.

Figure 2:
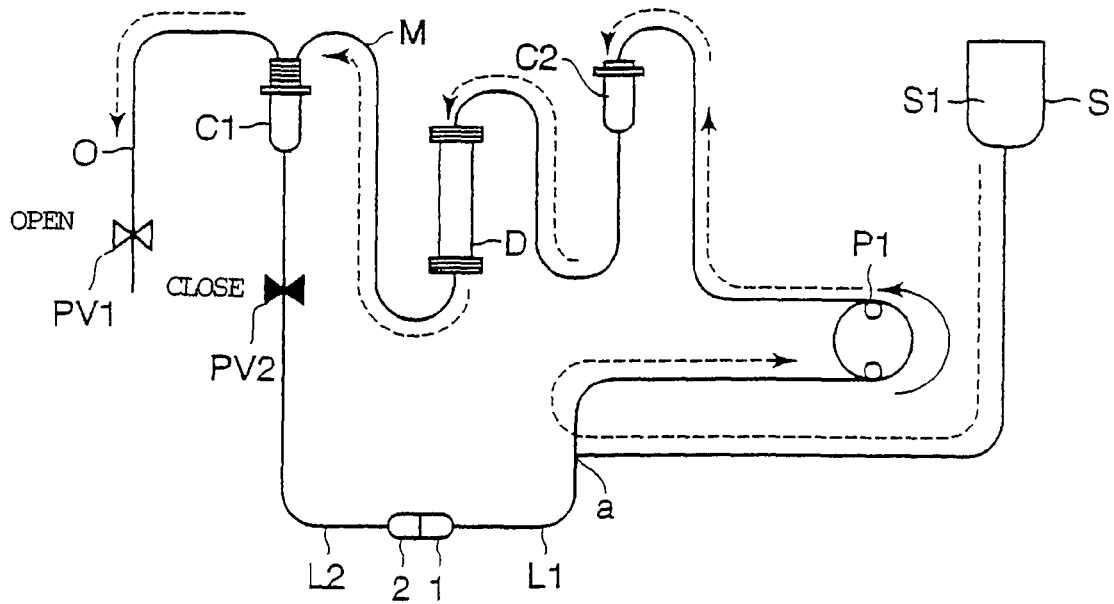
FIG. 2 is a schematic diagram showing an overflow step in a forward direction according to the present invention.

(b) FIG. 2 is a diagram showing a step of cleaning an arterial blood circuit, that is, an overflow step in a forward direction, in which bubbles and the circulating physiological saline in the circuit are discharged through the overflow line O. In the overflow step in the forward direction, the valve 1 is opened, the valve 2 is closed (the valve 2 is closed, so the physiological saline remains in a line from the valve 2 through an arterial blood circuit L1 and a venous blood circuit L2 to a branch point a), and the blood pump P1 is rotated forward at a preset speed of 100 to 300 mL/min, preferably about 200 mL/min, to send the physiological saline through a chamber C2, thereby allowing the circuit from the branch point a to the chamber C1 to be filled with the physiological saline and allowing bubbles in the blood circuit to pass through the overflow line O and the valve 1 in the stated order to be discharged. In this step, when a speed of the blood pump P1 is too low, it takes long, but when the speed thereof is too high, a pressure is applied to the overflow line through which the physiological saline is discharged and there is a risk of the dialyzer being applied with too much pressure. Therefore, the speed is preferably set within a range of 100 to 300 mL/min.

Figure 3:
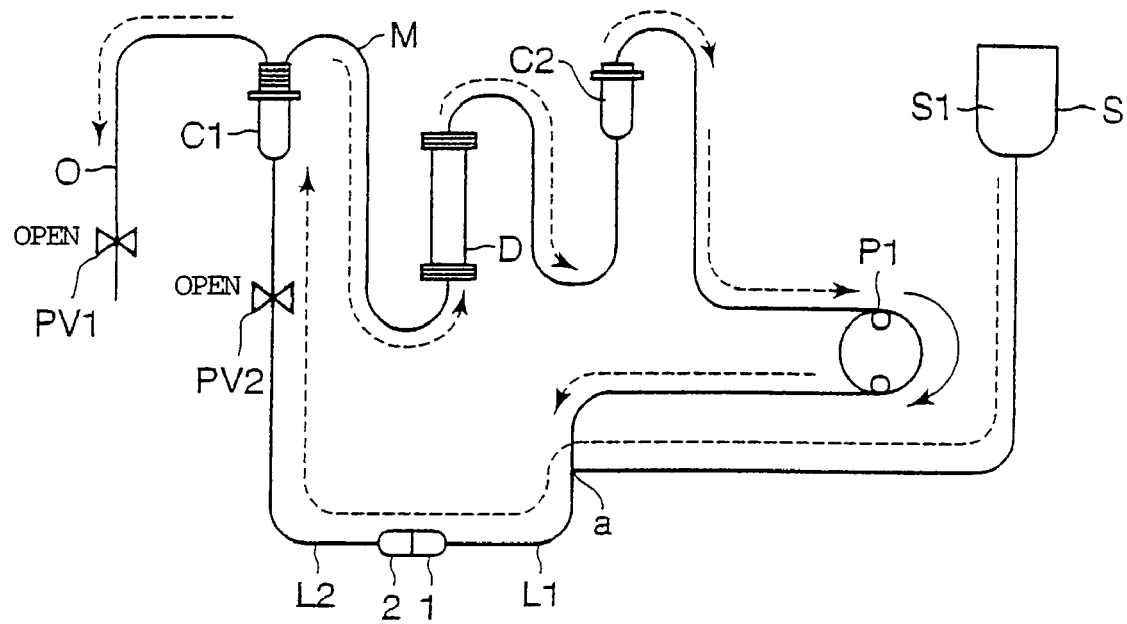
FIG. 3 is a schematic diagram showing an overflow step in a reverse direction according to the present invention.

(c) FIG. 3 shows a reverse direction re-circulation step of the overflow step. In the overflow step in a reverse direction, both the valves 1 and 2 are opened and the blood pump P1 is rotated backward at a speed of 10 to 50 mL/min, preferably about 20 mL/min, whereby bubbles accumulating in an upper portion of the arterial chamber C2 (and an upper portion of a dialyzer D) are discharged, and at the same time, a priming liquid is passed through the venous chamber C1 from the valve 2 through the blood pump P1, an arterial blood circuit L1, and the venous blood circuit L2, to be flown out of the overflow line O to the valve 1. This is because a floating speed of air is higher than a flow rate of the priming liquid (for example, 20 mL/min), and in the arterial chamber C2, a tube of a main line M is longer in a downward direction than a tube of the overflow line O, so the circulated bubbles are not sucked in the main line and are sucked in the overflow line O and flow in the overflow line O.

The speed of the blood pump P1 is made 10 to 50 mL/min. This is because by making the speed of the blood pump P1 lower than the floating speed of air expelled from the arterial chamber and flowing into the venous chamber, re-circulation of air is prevented. When the speed of the blood pump P1 is too high, recontamination of air is induced. When the speed thereof is too low, it takes too long time to expel the air.

Figure 4:
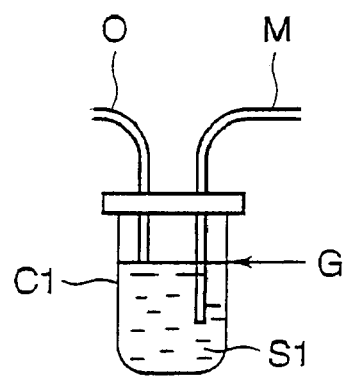
FIG. 4 is a schematic diagram showing a venous chamber according to the present invention.

FIG. 4 shows a structure of the venous chamber C1. During the step of the item (c) for priming, a space above a physiological saline S which is stored is restricted at a distal end position of the overflow line O to be secured. A floating speed of bubbles in the physiological saline (priming liquid), that is, bubbles discharged from the arterial chamber is higher than a suction speed (blood pump speed 10 to 50 mL/min) into the main pipe M immersed in the physiological saline, so the bubbles are not sucked into the main pipe M. Therefore, the bubbles float on a border surface G, that is, a liquid surface in the space to be discharged through the overflow line O positioned on the border surface G.

Figure 5:
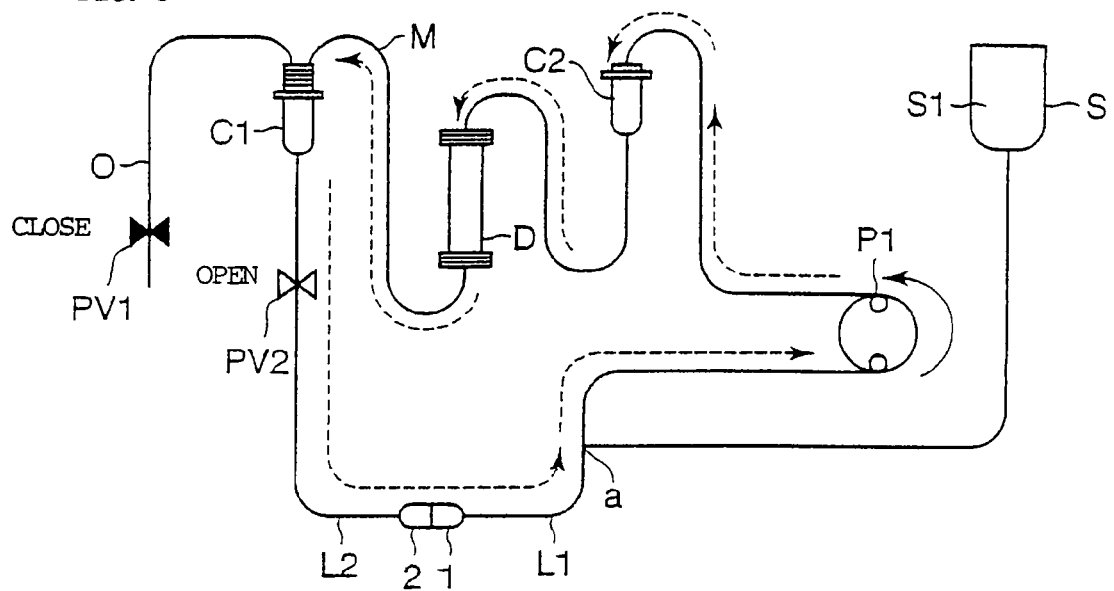
FIG. 5 is a schematic diagram showing a circulation step according to the present invention.

(d) FIG. 5 is an explanatory diagram showing a forward direction circulation step, which is embodied as occasion needs. In the circulation step, the valve 1 is closed and the valve 2 is opened. The blood pump P1 is rotated forward and the circulation is performed in the circuit. The circulation is performed from a line below the venous chamber C1 through the valve 2, the venous blood circuit L2, and the arterial blood circuit L1 to the blood pump P1, further through the arterial chamber C2 and the dialyzer D to the venous chamber C1. Fine bubbles existing in a line from a lower portion of the venous chamber C1 to an upper portion the arterial chamber C2 accumulate in the upper portion of the arterial chamber C2. Fine bubbles existing in a line from a lower portion of the dialyzer D to the upper portion of the venous chamber C1 accumulate in the venous chamber C1.

In this step, the fine bubbles accumulate in the chambers (C1 and C2). When the bubbles are in the line, thrombi are liable to be formed during the dialysis. It is required to prevent the thrombi from being formed and bubbles from entering a human body. The accumulating bubbles can be discharged by repeating the reverse direction re-circulation step and the forward direction circulation step.

According to the present invention, the following means may be added to the above-mentioned steps.

(e) In an apparatus according to claim 1, a supply pipe K is provided with a liquid shortage detector E and a supply pipe opening and closing valve PV3 (valve 3).

(f) The opening and closing valves 1, 2, and 3 and the blood pump P1 are connected to an operation control portion F for controlling operations of those.

(g) After the step of the item (c), the valve 1 and the valve 2 are opened and the blood pump P1 is operated to rotate forward, the priming liquid is supplied, and while circulation is performed, an excessive liquid is discharged through the overflow line O.

(h) The supply pipe K is provided with the liquid shortage detector E, liquid shortage is detected in the step of the item (c), and at the same time, the step proceeds to the step of the item (d).

(i) The supply pipe K is provided with the liquid shortage detector E, the liquid shortage is detected in the step of the item (g), and at the same time, the step proceeds to the step of the item (d).

(j) The supply pipe K is provided with the supply pipe opening and closing valve PV3 (valve 3).

Those additional steps may be appropriately combined with each of the above-mentioned steps.

By the priming method according to the present invention as described above, an operation of setting an installation direction of the chambers is not required. Further, it is possible to reliably conduct the priming for the entire blood circuit, to eliminate foreign substances and bubbles, and to simplify a dialysis operation.

The invention claimed is:

1. An automatic priming method, which is performed by rotating a blood pump forward and backward in a blood purification circuit in which a connection portion of an arterial blood circuit and a connection portion of a venous blood circuit are connected to form a circulation circuit in which the blood pump, an arterial chamber, a dialyzer operable to function as a blood purifier, and a venous chamber are arranged in the stated order, the venous chamber being connected to an overflow line having an overflow line valve which is operable for opening and closing said overflow line, a side of the venous blood circuit being provided with a venous blood circuit valve which is operable for opening and closing the venous blood circuit, the arterial-side blood circuit being connected to a storage container for storing a physiological saline as a priming liquid via a supply pipe continuous with the container at a physiological saline line branch portion located between the blood pump and the connection portion of the arterial blood circuit, the method comprising:

filling the venous blood circuit with the physiological saline with the blood pump being stopped, the overflow line valve and the venous blood circuit valve being opened, wherein, by a drop pressure in the physiological saline storage container, the physiological saline fills the venous chamber through the physiological saline line branch portion and the venous circuit closing valve, and is discharged together with bubbles through the overflow line and the overflow line valve;

discharging the bubbles and circulating physiological saline in the venous blood circuit through the overflow line by rotating the blood pump forward at a speed of 100 to 300 mL/min with the overflow line opening valve being opened and the venous circuit valve being closed, such that the physiological saline remains in a line portion from the venous circuit closing valve through the arterial blood circuit and the venous blood circuit to the physiological saline line branch portion, and the physiological saline is sent through the chamber, thereby allowing a part of the circuit from the physiological saline line branch point to the venous chamber to be filled with the physiological saline and bubbles in the blood circuit to be discharged through the overflow line and the overflow line valve;

rotating the blood pump backward at a speed of 10 to 50 mL/min with the overflow line valve and the venous circuit valve opened, thereby allowing bubbles accumulating in an upper portion of the arterial chamber and an upper portion of the dialyzer to be discharged, and simultaneously allowing the priming liquid to pass through the venous chamber from the venous circuit valve through the blood pump, the arterial blood circuit, and the venous blood circuit, to flow out of the overflow line through the overflow line valve.

2. An automatic priming method, which is performed by rotating a blood pump forward and backward in a blood purification circuit in which a connection portion of an arterial blood circuit and a connection portion of a venous blood circuit are connected to form a circulation circuit in which the blood pump, an arterial chamber, a dialyzer operable to function as a blood purifier, and a venous chamber are arranged in the stated order, the venous chamber being connected to an overflow line having an overflow line valve which is operable for opening and closing said overflow line, a side of the venous blood circuit being provided with a venous blood circuit valve which is operable for opening and closing the venous blood circuit, the arterial blood circuit being connected to a storage container for storing a physiological saline as a priming liquid via a supply pipe continuous with the container at a physiological saline line branch portion located between the blood pump and the connection portion of the arterial blood circuit, the method comprising:

filling the venous blood circuit with the physiological saline with the blood pump being stopped, the overflow line valve and the venous blood circuit valve being opened, wherein, by a drop pressure in the physiological saline storage container, the physiological saline fills the venous chamber through the physiological saline line branch portion and the venous circuit closing valve, and is discharged together with bubbles through the overflow line and the overflow line valve;

discharging the bubbles and circulating physiological saline in the venous blood circuit through the overflow line by rotating the blood pump forward at a speed of 100 to 300 mL/min with the overflow line opening valve being opened and the venous circuit valve being closed, such that the physiological saline remains in a line portion from the venous circuit closing valve through the arterial blood circuit and the venous blood circuit to the physiological saline line branch portion, and the physiological saline is sent through the chamber, thereby allowing a part of the circuit from the physiological saline line branch point to the venous chamber to be filled with the physiological saline and bubbles in the blood circuit to be discharged through the overflow line and the overflow line valve;

rotating the blood pump backward at a speed of 10 to 50 mL/min with the overflow line valve and the venous circuit valve opened, thereby allowing bubbles accumulating in an upper portion of the arterial chamber and an upper portion of the dialyzer to be discharged, and simultaneously allowing the priming liquid to pass through the venous chamber from the venous circuit valve through the blood pump, the arterial blood circuit, and the venous blood circuit, to flow out of the overflow line through the overflow line valve; and again rotating the blood pump forward with the overflow line valve closed and the venous circuit valve opened to perform circulation from a line extending from a lower portion of the venous chamber through the venous circuit valve, the venous blood circuit, and the arterial blood circuit (L1) to the blood pump (P1), further through the arterial chamber and the dialyzer to the venous chamber, such that fine bubbles existing in a line extending from an upper portion of the arterial chamber accumulate in the upper portion of the arterial chamber, and fine bubbles existing in a line extending from a lower portion of the dialyzer to an upper portion of the venous chamber accumulate in the venous chamber.

3. An automatic priming method according to claim 2, wherein:
the supply pipe is provided with a liquid shortage detector;
liquid shortage is detected during said rotating the blood pump backward; and
at a same time, said rotating the blood pump backward proceeds to said again rotating the blood pump forward.

4. An automatic priming method according to claim 1 or 2, wherein the supply pipe is provided with a supply pipe valve operable to open and close said supply pipe.

5. An automatic priming method according to claim 1 or 2, wherein the overflow line valve, the venous circuit valve, the supply pipe valve and the blood pump are connected to an operation control portion for controlling operations thereof.

6. An automatic priming method according to claim 1 or 2, further comprising operating the blood pump to rotate forward with the overflow line valve with the venous circuit valve being opened, such that the priming liquid is supplied, and while circulation is performed, an excessive liquid is discharged through the overflow line.

7. An automatic priming method according to claim 6, wherein:
the supply pipe is provided with a liquid shortage detector; and
liquid shortage is detected during said operating the blood pump to rotate forward.

8. An automatic priming method according to claim 1 or 2, wherein said venous chamber includes a main pipe connecting with said dialyzer, an end of a tube portion of said main pipe being immersed in the physiological saline contained in the venous chamber, a floating speed of bubbles in the physiological saline discharged from the arterial chamber being higher than a suction speed into the main pipe during said rotating the blood pump backward.

9. An automatic priming method according to claim 8, wherein the tube portion of said main pipe within said venous chamber is longer in a downward direction than a corresponding tube portion of the overflow line.

* * * * *